(12) United States Patent
Smola

(10) Patent No.: US 9,445,948 B2
(45) Date of Patent: Sep. 20, 2016

(54) SYSTEM FOR WOUND THERAPY

(71) Applicant: Hans Smola, Saarbrücken (DE)

(72) Inventor: Hans Smola, Saarbrücken (DE)

(73) Assignee: Paul Hartmann AG, Heidenheim (DE)

( * ) Notice: Subject to any disclaimer, the term of this patent is extended or adjusted under 35 U.S.C. 154(b) by 124 days.

(21) Appl. No.: 14/034,709

(22) Filed: Sep. 24, 2013

(65) Prior Publication Data

US 2014/0088527 A1    Mar. 27, 2014

Related U.S. Application Data

(60) Provisional application No. 61/705,304, filed on Sep. 25, 2012.

(30) Foreign Application Priority Data

Sep. 25, 2012 (EP) .................................... 12006687

(51) Int. Cl.
*A61F 13/00* (2006.01)
*A61M 1/00* (2006.01)
(Continued)

(52) U.S. Cl.
CPC ..... *A61F 13/00068* (2013.01); *A61F 13/0216* (2013.01); *A61M 1/0023* (2013.01);
(Continued)

(58) Field of Classification Search
CPC ............. A61F 13/00068; A61F 13/0216; A61F 2013/00089; A61F 2013/00217; A61F 2013/00221; A61F 2013/00727; A61F 2013/00744; A61F 2013/00748; A61F 2013/00753; A61F 13/02; A61F 13/0203; A61F 13/00; A61F 2013/00523; A61F 2013/00676; A61F 2013/00719; A61M 1/0023; A61M 1/0088; A61M 1/0096
See application file for complete search history.

(56) References Cited

U.S. PATENT DOCUMENTS 5,465,735 A * 11/1995 Patel .............................. 128/888
5,645,081 A    7/1997 Argenta et al.
(Continued)

FOREIGN PATENT DOCUMENTS

CA    2 808 263 A1    2/2012
EP    0 594 034 A1    4/1994
(Continued)

OTHER PUBLICATIONS

Tsukasa Isago, Motohiro Nozaki, Yuji Kikuchi, Takashi Honda and Hiroaki Nakazawa. Negative-Pressure Dressings in the Treatment of Pressure Ulcers. The Journal of Dermatology. vol. 30, Issue 4, pp. 299-305, Apr. 2003.*

(Continued)

*Primary Examiner* — Adam Marcetich
(74) *Attorney, Agent, or Firm* — Jason D. Voight

(57) ABSTRACT

In wound therapy, a combination of negative pressure therapy and subsequent therapy in a preferably moist or moist-wet medium without use of negative pressure reduces costs and improves therapeutic results. Thus, the present invention involves a method for treatment of a wound by therapy having a first segment, in which negative pressure wound therapy is performed, and a subsequent, second segment, in which wound therapy is conducted using a wound dressing without creating a negative pressure. The wound dressing for the second segment has an absorbent body with a superabsorbent polymer. The invention also relates to a device for conducting negative pressure wound therapy and a wound dressing for use in such method, and further to a kit including such a device and wound dressing.

20 Claims, 3 Drawing Sheets

(51) Int. Cl.
*A61M 27/00* (2006.01)
*A61F 13/02* (2006.01)

(52) U.S. Cl.
CPC ......... *A61M1/0088* (2013.01); *A61M 1/0096* (2014.02); *A61F 2013/00089* (2013.01); *A61F 2013/00217* (2013.01); *A61F 2013/00727* (2013.01); *A61F 2013/00748* (2013.01); *A61F 2013/00753* (2013.01)

(56) References Cited

U.S. PATENT DOCUMENTS

| | | | |
|---|---|---|---|
| 6,169,223 B1* | 1/2001 | Mahr et al. | 602/56 |
| 2005/0070835 A1* | 3/2005 | Joshi | 602/41 |
| 2005/0215932 A1* | 9/2005 | Sigurjonsson et al. | 602/54 |
| 2007/0027414 A1* | 2/2007 | Hoffman | A61M 1/0088 602/2 |
| 2008/0208147 A1* | 8/2008 | Argenta et al. | 604/290 |
| 2008/0312572 A1* | 12/2008 | Riesinger | 602/43 |
| 2010/0159192 A1* | 6/2010 | Cotton | 428/137 |
| 2010/0262090 A1* | 10/2010 | Riesinger | 604/304 |
| 2010/0305490 A1* | 12/2010 | Coulthard et al. | 602/43 |
| 2011/0004172 A1 | 1/2011 | Eckstein et al. | |
| 2011/0054375 A1 | 3/2011 | Smola | |
| 2011/0230848 A1* | 9/2011 | Manwaring | A61M 1/0088 604/290 |
| 2011/0275972 A1* | 11/2011 | Rosenberg | A61F 13/00008 602/46 |
| 2011/0313373 A1 | 12/2011 | Riesinger | |
| 2012/0046589 A1 | 2/2012 | Eckstein et al. | |
| 2012/0059294 A1* | 3/2012 | Schubert et al. | 601/46 |
| 2012/0095380 A1* | 4/2012 | Gergely et al. | 602/45 |
| 2012/0095419 A1* | 4/2012 | Riesinger | 604/319 |

FOREIGN PATENT DOCUMENTS

| | | |
|---|---|---|
| WO | 2009/021523 A1 | 2/2009 |
| WO | 2009/086580 A1 | 7/2009 |

OTHER PUBLICATIONS

Gupta, Subhas; Baharestani, Mona; Baranoski, Sharon; de Leon, Jean; Engel, Scott J.; Mendez-Eastman, Susan; Niezgoda, Jeffery A.; Pompeo, Matthew Q. Guidelines for Managing Pressure Ulcers with Negative Pressure Wound Therapy. Advances in Skin & Wound Care. Nov./Dec. 2004—vol. 17—Issue—pp. 1-16.*
Gupta; Subhas and Ichioka; Shigeru. Optimal use of negative pressure wound therapy in treating pressure ulcers. International Wound Journal. vol. 9, Issue Supplement s1, pp. 8-16, Aug. 2012. Article first published online: Jun. 22, 2012. DOI: 10.1111/j.1742-481X.2012.01012.x.*
Ratliff, Catherine R. Negative-Pressure-Wound Therapy. Advance Healthcare Network for NPs and PAs. vol. 12 •Issue 7 • p. 47. Posted Jul. 1, 2004. http://nurse-practitioners-and-physician-assistants.advanceweb.com/Article/Negative-Pressure-Wound-Therapy.aspx. Accessed Nov. 18, 2015.*

* cited by examiner

S100A8

S100A9

SYSTEM FOR WOUND THERAPY

This application claims priority to Provisional Application Ser. No. 61/705,304 and European Patent Application No. EP12006687, both filed Sep. 25, 2012, the entire disclosures of which are incorporated by reference herein.

This invention relates to wound therapy and to devices/systems for wound therapy.

Negative pressure wound therapy (NPWT), also known as topical negative pressure (TNP) or vacuum assisted closure (VAC) treatment, has been known for a long time, but is finding increasing application since the mid/late-1990s. It typically involves a wound filling material being placed in the wound, the wound field being covered with a film and a negative pressure being created in the wound space using a drainage tube and a vacuum pump. The wound filling material supports a uniform distribution of pressure across the wound. The negative pressure ensures effective wound cleansing through removal of wound exudate. Promoting the formation of granulation tissue and reducing wound edema formation are further advantages. Negative pressure wound therapy, as implied by its alternative designation of VAC, is typically carried through to wound closure. Wound closure is generally considered to be achieved when there is a layer of epidermis over the former wound site. Wound closure can be achieved through healing processes or through surgical interventions.

Negative pressure wound therapy is especially used for acute or chronic wounds, for example ulcers (e.g., pressure ulcers, diabetic, neuropathic or venous insufficiency ulcers), traumatic wounds, therapy resistant wounds, infected wounds, postoperative wounds, explored fistulas and also skin flaps and skin grafts. Chronic wounds are characterized by slowed or nonexistent healing.

Negative pressure wound therapy devices are accordingly known in the prior art. For instance, WO 1993/009727 A1 describes a device for promoting the healing of wounds by the application of negative pressure to the area of skin including and surrounding the wound. The device described in WO 1993/009727 A1 comprises vacuum means for creating the negative pressure; an airtight wound covering operatively associated with the vacuum means; and also a wound dressing for positioning on the wound within the airtight covering. The wound dressing preferably comprises an open-cell polymer foam, for example polyester foam. In addition to the use of open-cell polymer foam, other materials have been described for producing wound dressings for use in negative pressure wound therapy.

Units for negative pressure wound therapy are also commercially available and range from small, portable units, which allow patients a certain degree of mobility, up to units for hospital use, for instance in long-term care facilities.

Disadvantages cited against negative pressure wound therapy include primarily the increased hardware requirements and the associated increased costs as well as patient inconvenience, especially impaired mobility on the part of the patient. Moreover, negative pressure wound therapy can be a painful experience for patients.

It is an object of the present invention to provide a form of wound therapy which exerts a positive influence on the physiological state of a wound. It is a further object to provide a form of wound therapy which minimizes the inconvenience to the patient. It is also an object to improve the cost side of wound therapy without, however, compromising the clinical efficiency of wound therapy or else to even improve the clinical efficiency, and to provide systems which facilitate such an improved wound therapy.

It was found that, surprisingly, a combination of negative pressure therapy and subsequent therapy in a preferably moist or moist-wet medium without use of negative pressure not only reduces costs, but also improves therapeutic results. More particularly, the formation of granulation tissue was unexpectedly discovered to improve over negative pressure therapy alone, within the same overall treatment time.

Moreover, the patient was less impaired compared with conventional negative pressure wound therapy, especially with regard to patient pain and mobility.

The present invention accordingly comprises in a first aspect a method for treatment of a wound by therapy, wherein said wound therapy comprises a first segment of therapy, in which negative pressure wound therapy is performed, and a subsequent, second segment of therapy, in which wound therapy is conducted using a wound dressing without creating a negative pressure, wherein said wound dressing comprises an absorbent body comprising a swellable polymer, which is a superabsorbent polymer. In other words, the present invention in this first aspect relates to the treatment of wounds on the human or animal body by therapy, wherein said therapy comprises negative pressure wound therapy, wherein said treatment by therapy comprises a first segment of therapy, in which negative pressure wound therapy is performed using a device for conducting negative pressure wound therapy, and a subsequent, second segment of therapy, in which said treatment by therapy is conducted using a wound dressing without creating a negative pressure, wherein said wound dressing comprises an absorbent body comprising a superabsorbent polymer. The wound dressing used in the second segment of therapy is generally referred to as "the second wound dressing" in the following.

A device used for conducting negative pressure wound therapy will hereinafter also be referred to simply as negative pressure therapy device.

The present invention further comprehends the use of a device for negative pressure wound therapy in the treatment of wounds on the human or animal body by therapy, wherein said treatment by therapy comprises a first segment of therapy, in which negative pressure wound therapy is performed using said device, and a subsequent, second segment of therapy, which is conducted using a wound dressing without creating a negative pressure, wherein the wound dressing comprises an absorbent body comprising a swellable polymer, which is a superabsorbent polymer.

The present invention provides in a second aspect a wound dressing for wound therapy—preferably in a moist or moist-wet environment—wherein wound therapy comprises a first segment of therapy, in which wound therapy is conducted by creating negative pressure, and a subsequent, second segment of therapy, in which wound therapy is preferably conducted in a moist or moist-wet environment by using said wound dressing without creating a negative pressure. More particularly, the present invention relates to a wound dressing for use in the treatment of wounds on the human or animal body by therapy, wherein said wound dressing comprises an absorbent body comprising a swellable polymer, which is a superabsorbent polymer, wherein said treatment by therapy comprises a first segment of therapy, in which wound therapy is conducted using negative pressure, and a subsequent, second segment of therapy, in which said treatment by therapy is conducted using said wound dressing without creating a negative pressure.

In other words, according to the second aspect of the invention, the present invention relates to an article of manufacture for use in the treatment of wounds on the human or animal body by therapy, wherein said article of manufacture comprises a wound dressing, and wherein said wound dressing comprises an absorbent body comprising a superabsorbent polymer, wherein said treatment by therapy comprises a first segment of therapy, in which negative pressure wound therapy is conducted using a device for negative pressure wound therapy, and a subsequent, second segment of therapy, in which said treatment by therapy is conducted using said wound dressing without creating a negative pressure.

According to a third aspect, the present invention provides a kit of parts comprising a device for conducting negative pressure wound therapy and a wound dressing for wound therapy—preferably in a moist or moist-wet environment—wherein wound therapy comprises a first segment of therapy, in which wound therapy is conducted using the device by creating negative pressure, and a subsequent, second segment of therapy, in which wound therapy is preferably conducted in a moist or moist-wet environment by using said wound dressing without creating a negative pressure. In other words, according to the third aspect of the present invention, the present invention relates to an article of manufacture for use in the treatment of wounds on the human or animal body by therapy, wherein said article of manufacture comprises a device for negative pressure wound therapy and a wound dressing, and wherein said wound dressing comprises an absorbent body comprising a swellable polymer, which is a superabsorbent polymer, wherein said treatment by therapy comprises a first segment of therapy, in which negative pressure wound therapy is conducted using a device for negative pressure wound therapy, and a subsequent, second segment of therapy, in which said treatment by therapy is conducted using said wound dressing without creating a negative pressure.

The present invention further comprehends the use of a kit of parts comprising a device for negative pressure wound therapy and a wound dressing in the treatment of wounds on the human or animal body by therapy, wherein said wound dressing comprises an absorbent body comprising a swellable polymer, which is a superabsorbent polymer, wherein said treatment by therapy comprises a first segment of therapy, in which negative pressure wound therapy is conducted using said device for negative pressure wound therapy, and a subsequent, second segment of therapy, in which said treatment by therapy is conducted using said wound dressing without creating a negative pressure.

The present invention further provides a method for treatment of wounds on the human or animal body by therapy, said method comprising
i) a first segment of therapy, in which negative pressure wound therapy is conducted using a device for negative pressure wound therapy, wherein said device for conducting negative pressure wound therapy comprises
  (a) an air impermeable covering material for airtight enclosure of the wound and its surroundings to form a wound space,
  (b) means for providing fluid communication between said wound space and a negative pressure source outside said covering material so that a negative pressure can be established in said wound space and liquids can be aspirated out of said wound space,
  (c) a first wound dressing facilitating an essentially uniform distribution of said negative pressure in said wound space,
ii) a subsequent, second segment of therapy, in which said treatment by therapy is conducted, preferably in a moist or moist-wet environment, by using a second wound dressing without creating a negative pressure, wherein said second wound dressing comprises an absorbent body comprising a superabsorbent polymer.

The first wound dressing preferably comprises or is a wound dressing comprising an open-cell foam, for example an open-cell polyurethane foam. In an alternative embodiment, however, the first wound dressing used for the first segment of therapy can also be an absorbent body comprising a swellable polymer, especially a superabsorbent polymer.

The present invention also provides, in particular, a method for treatment of wounds on the human or animal body by therapy, said method comprising
i) a first segment of therapy, in which negative pressure wound therapy is conducted using a device for negative pressure wound therapy, for inflammation control and/or edema mobilization in the wound region, wherein said device for conducting negative pressure wound therapy comprises
  (a) an air impermeable covering material for airtight enclosure of the wound and its surroundings to form a wound space,
  (b) means for providing fluid communication between said wound space and a negative pressure source outside said covering material so that a negative pressure can be established in said wound space and liquids can be aspirated out of said wound space,
  (c) a first wound dressing facilitating an essentially uniform distribution of said negative pressure in said wound space,
ii) a subsequent, second segment of therapy, in which a second wound dressing is used to effect an enhanced stimulation of the formation of granulation tissue in the wound region,
and/or
an enhanced stimulation of neovascularization in the wound region,
and/or
an enhancement in the fibroblast density in the surficial granulation tissue of a wound,
each without creating a negative pressure,
wherein said second wound dressing comprises an absorbent body comprising a superabsorbent polymer.

The present invention finally provides a kit of parts comprising a device for negative pressure wound therapy and a wound dressing, for use in the treatment of wounds on the human or animal body by therapy, wherein said wound dressing comprises an absorbent body comprising a superabsorbent polymer, wherein said treatment by therapy comprises a first segment of therapy, in which negative pressure wound therapy is conducted using said device, and a subsequent, second segment of therapy, in which said treatment by therapy is conducted using said wound dressing without creating a negative pressure. The kit preferably also comprises instructions for carrying out said treatment of a wound by therapy in accordance with the present invention.

DETAILED DESCRIPTION OF THE INVENTION

It was found that, surprisingly, the length of negative pressure wound therapy can be significantly shortened and replaced by wound therapy using the wound dressing of the present invention, i.e., preferably in a moist or moist-wet environment, without application of negative pressure, while—contrary to all expectations—the formation of granulation tissue is not sacrificed but actually improved. Improved clinical results were achieved as well as cost savings and improved patient compliance.

In particular, the therapy scheme of the present invention was unexpectedly found to provide
enhanced stimulation of formation of granulation tissue in the wound region, beyond the degree normally achievable in negative pressure wound therapy;
an enhanced stimulation of neovascularization in the wound region; and/or
a distinct increase in fibroblast density in the surficial granulation tissue of a wound.

The present invention accordingly provides a wound dressing for use in the method of treatment of wounds on the human or animal body by therapy, wherein said wound dressing comprises an absorbent body comprising a superabsorbent polymer, wherein said wound dressing is applied on abatement of the inflammatory phase following a preceding negative pressure wound therapy. The present invention accordingly also provides a method of treatment of wounds on the human or animal body by therapy comprising applying a wound dressing on abatement of the inflammatory phase following a preceding negative pressure wound therapy, wherein said wound dressing comprises an absorbent body comprising a superabsorbent polymer.

The present invention further provides a method of inflammation control and/or edema mobilization in the treatment of wounds on the human or animal body by therapy, the treatment of wounds comprising a first phase of therapy followed by a second phase of therapy, wherein said first phase of therapy comprises a negative pressure wound therapy using a device for negative pressure wound therapy, and wherein said second phase of therapy comprises use of a wound dressing comprising an absorbent body comprising a superabsorbent polymer without creating a negative pressure. The present invention thus provides a method of inflammation control and/or edema mobilization in the treatment of wounds on the human or animal body by therapy comprising the use of a wound dressing comprising an absorbent body comprising a superabsorbent polymer, following negative pressure wound therapy. The terms "segment of therapy" and "phase of therapy" herein are used interchangeably.

The present invention further provides a method for enhanced stimulation of the formation of granulation tissue in a wound region in the therapy of wounds on the human or animal body by therapy, following negative pressure wound therapy, comprising the use of a wound dressing comprising an absorbent body comprising a superabsorbent polymer.

Figure 2:
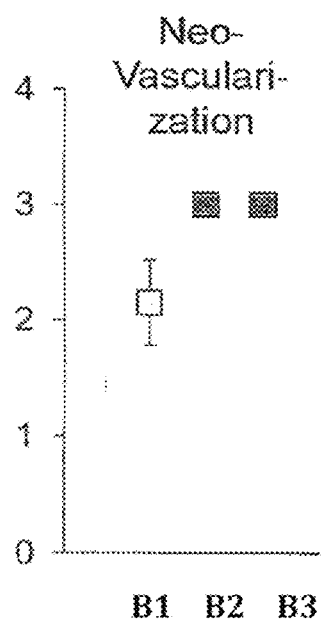
FIG. 2 illustrates neovascularization for the invention (B2, B3) in relation to negative pressure therapy (B1).

The present invention further provides a method for enhanced stimulation of the neovascularization in a wound region following a negative pressure wound therapy in the therapy of wounds on the human or animal body by therapy, comprising use of a wound dressing comprising an absorbent body comprising a superabsorbent polymer. FIG. 2 below illustrates advantageous stimulation of neovascularization.

Figure 3:
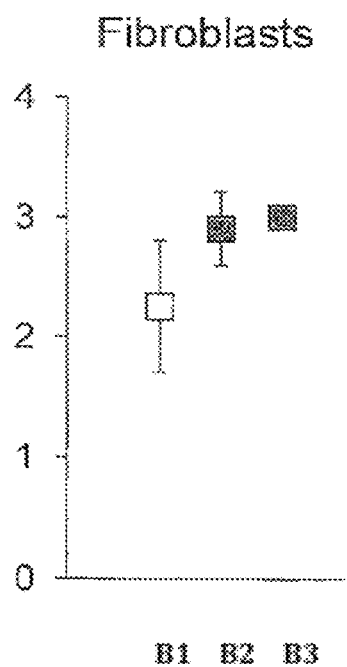
FIG. 3 illustrates formation of fibroblasts for the invention (B2, B3) in relation to negative pressure therapy (B1).
Figure 4:
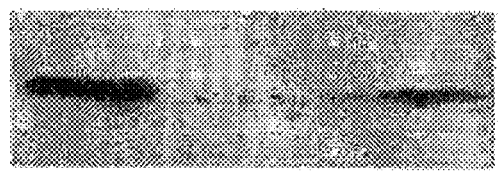
FIG. 4 illustrates the presence of mediator proteins in wound exudate and the binding thereof by a polymer of the invention.
Figure 4:
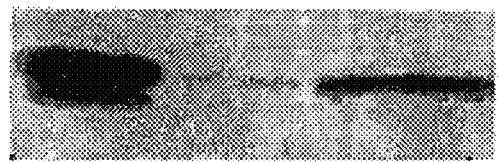

The present invention further provides a method for increasing fibroblast density in the surficial granulation tissue of a wound following negative pressure wound therapy in the therapy of wounds on the human or animal body by therapy, comprising use of a wound dressing which comprises an absorbent body comprising a superabsorbent polymer. FIG. 3 below illustrates an increase of the fibroblast formation.

The "use of a wound dressing" as used herein shall encompass the application of the wound dressing to a wound or packing out deep wounds.

The literature describes three essential healing phases of a wound, especially in the case of wounds involving tissue loss. They include the inflammatory or exudative phase for blood coagulation and wound cleansing (phase 1, cleansing phase), the proliferative phase for construction of granulation tissue (phase 2, granulation phase) and the differentiation phase for epithelization and scar formation (phase 3, epithelization phase).

The inflammatory phase typically occurs directly after wound formation. It is characterized by vascular constriction, activation of the coagulation cascade and complex immunological processes. The release of chemoattractive substances (chemokines for example) can trigger a local inflammatory reaction. There are four essential signs of inflammation: edema, exudation, reddening and pain. The surrounding vessels can expand, and inflammatory cells can migrate into the site of inflammation. They can eliminate microorganisms and tissue necroses. This can effect cleansing of the wound.

The subsequent proliferation or granulation phase involves the construction of new tissue with vascular invasion and defect repair by granulation tissue. This is a basic prerequisite for later epithelization. Fibroblasts from the surrounding tissue can migrate into the fibrin mesh and use it as a provisional matrix. The construction of collagen fibers starts. The provisional scaffolding of fibrin is replaced by the granulation tissue. The simultaneously ongoing angiogenesis supplies the granulation tissue with invading capillaries and vessels.

The start of the differentiation or restructuring phase is typically the start of the maturation of the collagenic fibers. The wound contracts as fibroblasts are transformed into fibrocytes and also myofibroblasts. This causes the scar tissue to shrink and the wound to become smaller. Epithelization from the edge of the wound concludes the wound healing process.

The first segment of therapy preferably merely comprehends the inflammatory phase or part thereof. In other words, abatement or conclusion of the inflammatory phase preferably signals the end of said first segment of therapy. Abatement of the inflammatory phase is apparent to the physician from the abatement of one or more of the symptoms of inflammation: edema, exudation, reddening and pain. The first segment of therapy is preferably terminated before visible granulation.

The duration of the first segment of therapy depends on the individual circumstances. However, successes have been achieved when the first segment of therapy extends over a period of just 1, 2, 3, 4, 5, 6, 7 or 8 days for example, e.g. for between 3 and 7 or 4 and 6 days, especially 4 days. This time span is shorter than the typical duration of a negative pressure wound therapy. Negative pressure wound therapy need no longer be conducted through to wound closure, in particular.

The second segment of therapy must likewise be adjusted to the individual circumstances, can for example extend with advantage for a period of 1 to 1000 days, preferably from one or two to one hundred days, e.g., one to eight days, or three to twenty days, or four to ten days.

A combination of a four-day first segment of therapy with a likewise four-day second segment of therapy proved advantageous in an experiment. As will be shown later with reference to figures, this alternative to a traditional 8-day negative pressure wound therapy gives better wound therapy results.

The second segment of therapy preferably follows immediately on from the first segment of therapy.

The negative pressure wound therapy device to be used according to the present invention can be a device known from the prior art. Advantageously, the device for conducting negative pressure wound therapy comprises
(a) an air impermeable covering material for airtight enclosure of the wound and its surroundings to form a wound space,
(b) means for providing fluid communication between said wound space and a negative pressure source outside said covering material so that a negative pressure can be established in said wound space and liquids can be aspirated out of said wound space,
(c) a wound dressing preferably comprising an open-cell foam. The wound dressing used in the negative pressure device/the first segment or phase of therapy is generally referred to as "the first wound dressing" herein.

The negative pressure therapy device which can be used according to the present invention comprises a covering material (a) for airtight enclosure of the wound. Here "airtight enclosure" is not to be understood as meaning that there is no gas exchange whatsoever between the wound space and its surroundings. Rather, "airtight enclosure" in this context is to be understood as meaning that the negative pressure needed for negative pressure wound therapy can be maintained. Therefore, covering materials having minimal gas permeability can also be used as long as the negative pressure necessary for negative pressure wound therapy can be maintained.

The airtight covering material can be for example in the form of a shell consisting of a firm material or in the form of a flexible foil. Combinations of these are also conceivable. In a preferred embodiment of the present invention, the covering material for airtight enclosure of the wound comprises a water-insoluble polymer, or a metal foil. The covering material is preferably from 10 µm to 10 000 µm and especially from 25 µm to 100 µm in thickness.

In a preferred embodiment of the present invention, said covering material (a) comprises a water-insoluble polymer. The solubility of the water-insoluble polymer is preferably 10 mg/l or less, more preferably 1 mg/ml or less and especially 0.0001 to 1 mg/ml (determined using the column elution method of EU Directive CD67-548-EEC, Annex V Chapter A6). Examples are polyurethane, polyester, polypropylene, polyethylene, polyamide or polyvinyl chloride, polyorganosiloxane (silicone), or a mixture thereof. The polymers referred to here are preferably in non-cellular form. In a preferred embodiment, the covering material has a water vapor transmission rate of 100 to 2500 $g/m^2 \times 24$ h, more preferably of 500 to 2000 $g/m^2 \times 24$ h, even more preferably of 800 to 1600 $g/m^2 \times 24$ h and especially 1050 to 1450 $g/m^2 \times 24$ h, determined as per DIN EN 13726-2 at 23° C. and 85% relative humidity.

Ready-made products having the aforementioned properties can also be used as covering material. Hydrofilm® polyurethane film (Paul Hartmann AG, Germany) or Visulin® polyurethane film (Paul Hartmann AG, Germany) has proved to be a suitable covering material for the negative pressure therapy device to be used according to the present invention.

The covering material is typically secured in the wound environment or at the wound edge so as to ensure an airtight wound closure. It can be advantageous here for the covering material to be self-adhesive all over or to have a self-adhesive edge. Alternatively, securement and sealing can be effected with an adhesive film, with a liquid adhesive or with a sealant for example. However, it is also possible for the covering material to be merely held on the wound by the negative pressure created by the negative pressure treatment.

The negative pressure therapy device of the present invention comprises means (b) for providing fluid communication between said wound space and a negative pressure source outside said covering material so that a negative pressure can be established in said wound space and liquid can be aspirated out of said wound space.

The expression "negative pressure in the wound space" in connection with the invention designates an air pressure reduced within the wound bandage compared with the ambient pressure (atmospheric air pressure). By "within the wound bandage" is meant the interspace formed between the covering material and the wound.

Fluid communication can be established for example with a connecting line and/or with a negative pressure port.

In one embodiment, the means for operatively associating the wound space with a negative pressure source outside the covering material comprises at least one connecting line. The at least one connecting line can pass through the covering material. Alternatively, the at least one connecting line can pass underneath the edge of the covering material. In either case, the point of passage must be sealed off airtight, so the desired negative pressure in the bandage can be maintained. Examples of suitable sealing materials are an adhesive film, an adhesive composition or an adhesive strip.

The connecting line may comprise a piece of tubing, a tube or some other body having a void space for example. Silicone drainage tubing is an example of a suitable piece of tubing.

In a further embodiment, the means for operatively associating the wound space with a negative pressure source outside the covering material comprises a negative pressure port which can be secured to either the inside or the outside surface of the covering material, in which case the covering material has suitable apertures. This embodiment again requires that care be taken to ensure an airtight seal between the port inside or the port outside. The seal can be established for example using an adhesive film, an adhesive composition or an adhesive strip. It is also conceivable for the port itself to have appropriate securing means, for example adhesive surfaces.

In a preferred embodiment, the covering material (a) and the means (b) for providing fluid communication between the wound space and a negative pressure source outside the covering material will already be available for use connected to each other.

In addition to constituents (a) and (b) described above, the negative pressure therapy device of the present invention further comprises constituent (c), the (first) wound dressing, which comprises or consists of open-cell foam.

In the context of this application, the term "open-cell" is to be understood as meaning that foam (c) contains not less than 60% of open cells, preferably not less than 90% of open cells, more preferably not less than 98% of open cells, especially essentially 100% of open cells, based on the total number of cells.

The (first) wound dressing (c) of the negative pressure device also facilitates for example an essentially uniform distribution of the negative pressure in the wound space.

In a preferred embodiment, the open-cell foam is a polyurethane foam obtainable by reacting a mixture comprising components (i) polyisocyanate, (ii) polyol, preferably polyester polyol, (iii) blowing agent, and (iv) catalyst.

Any generally/commonly known aliphatic, cycloaliphatic and/or especially aromatic polyisocyanates can be used as polyisocyanates (i-PUR). The polyurethanes are suitably prepared using for example diphenylmethane diisocyanate (MDI), especially 4,4'-diphenylmethane diisocyanate (4,4'-MDI), mixtures of monomeric diphenylmethane diisocyanates and higher-nuclear homologs of diphenylmethane diisocyanate (PMDI), tetramethylene diisocyanate (TMDI), hexamethylene diisocyanate (HDI), tolylene diisocyanate (TDI) or mixtures thereof.

Polyols such as polyetherols and/or polyesterols are typically used as isocyanate-reactive compounds (ii-PUR). Preference is given to using polyester polyols in component (ii-PUR). The (ii-PUR) polyesterols used are generally prepared by condensing polyfunctional alcohols, preferably diols, having 2 to 12 carbon atoms, preferably 2 to 6 carbon atoms, with polyfunctional carboxylic acids having 2 to 12 carbon atoms, preferably 4 to 8 carbon atoms. Examples of suitable acids are succinic acid, glutaric acid, adipic acid, phthalic acid, isophthalic acid, and/or terephthalic acid and mixtures thereof. Adipic acid is particularly preferred. Examples of suitable di- and polyhydric alcohols are ethanediol, diethylene glycol, 1,4-butanediol, 1,5-pentanediol, and/or 1,6-hexanediol and mixtures thereof. 1,4-Butanediol is particularly preferred. The (ii-PUR) compounds can be used in admixture with crosslinking and/or chain-extending agents.

Useful catalysts (iv-PUR) are compounds which increase the rate of the reaction of the (i-PUR) component with the (ii-PUR) component. Examples include tertiary amines and/or organic metal compounds, especially tin compounds. The following compounds can be used as catalysts for example: triethylenediamine, aminoalkyl- and/or aminophenylimidazoles and/or tin(II) salts of organic carboxylic acids. Catalysts are generally used in an amount of 0.1 to 5 wt % based on the weight of component (ii-PUR).

Commonly/generally known chemically or physically acting compounds can be used as blowing agents (iii-PUR). Water may preferably be used as the physically acting blowing agent; it reacts with the isocyanate groups to form carbon dioxide. Examples of physical blowing agents are (cyclo)aliphatic hydrocarbons, preferably those of 4 to 8, more preferably 4 to 6 and especially 5 carbon atoms, partially halogenated hydrocarbons or ethers, ketones or acetates. The amount of blowing agent used depends on the target density of the foam. The different blowing agents can be used singly or in any desired mixtures with each or one another. It is particularly preferable to use only water as blowing agent, generally in an amount of 0.1 to 5 wt %, especially of 2.5 to 4 wt %, based on the weight of component (ii-PUR). Physical blowing agents are preferably used in an amount of <0.5 wt %, based on the weight of component (ii-PUR).

The reaction is optionally effected in the presence of (v-PUR) auxiliary and/or added substances, for example fillers, cell regulators, cell openers, surfactants and/or stabilizers against oxidative, thermal or microbial degradation or aging.

The open-cell polyurethane foam is preferably obtained by reacting a mixture comprising or consisting of the following components:
(i) polyisocyanate selected from MDI, PMDI, TDI and/or HDI, (ii) polyester polyol, wherein the polyester polyol is preferably obtainable by reacting a dicarboxylic acid of 4 to 8 carbon atoms with a dialcohol having 2 to 6 carbon atoms, and/or preferably has a weight average molecular weight of 500 to 4000 g/mol, (iii) blowing agent, and (iv) catalyst.

The open-cell foam, especially polyurethane foam, preferably has a tensile strength between 80 kPa and 300 kPa, as measured in accordance with DIN 53571, after three-day immersion in bovine serum.

The open-cell foam, especially polyurethane foam, preferably has an air permeability of 1000 to 8000 l/(m² sec), as measured in accordance with DIN EN ISO 9237.

The (first) wound dressing (c) of the negative pressure device may comprise silver in the form of silver ions or in the form of atomic silver. Preferably, there is a coating of silver on the (first) wound dressing. Alternatively, there is a dispersion of silver within the (first) wound dressing. In the case of open-cell foams, for example, silver may even be part of the curable composition. The silver content of foam (c) is preferably from 0.000001 to 0.1 wt % and more preferably from 0.0001 to 0.01 wt %, based on the overall weight of foam (c).

In a preferred embodiment of the present invention, wound dressing (c), especially the open-cell foam, is from 1 to 50 mm and especially from 15 mm to 30 mm in thickness.

In a preferred embodiment of the present invention, the negative pressure wound therapy device comprises at least one wound contact layer for incorporation between wound dressing (c) and the wound surface. The additional wound contact layer can be associated with said wound dressing (c) in an adhering manner or in a nonadhering manner. Any wound contact layer known from the prior art can be used in principle provided it ensures passage of wound exudate and has no propensity to intergrow with or stick to the wound tissue. Hydrotüll®, Atrauman® and Atrauman Ag® ointment dressings from Paul Hartmann AG (Germany) are particularly suitable wound contact layers.

In a further embodiment, negative pressure wound therapy devices comprising as wound dressing (c) an open-cell foam based on a cross-linked polyorganosiloxane can also be used. One advantage of the open-cell foam based on a cross-linked polyorganosiloxane is that it provides a soft wound dressing for negative pressure wound therapy and ensures a uniform distribution of pressure onto the wound ground. Providing a soft wound dressing and ensuring a uniform distribution of pressure ensures that the negative pressure treatment is carried out gently as well as efficaciously.

In a further embodiment, the negative pressure wound therapy device comprises at least one additional pressure distribution layer between wound dressing (c) and covering material (a). The advantage of an additional pressure distribution layer can be that the pressure exerted by the bandage on the wound ground is even more uniformly distributable by using the pressure distribution layer. The pressure distribution layer can further store and/or conduct additional wound exudate.

The additional pressure distribution layer can consist of a wholly or partly open-cell foam, a spacer knit, of a textile layer, of a structured gel, or of a pervious layer of nonwoven. Suitable textile layers include ribbon gauzes with tucked-in folded ends, or lattice tulles. The additional pressure distribution layer may be configured to allow liquid, such as wound exudate, pass through it. To this end, the pressure distribution layer may contain suitable channels or apertures, or consist of a material that is permeable for liquids.

The above considerations regarding preferred embodiments of points (a) to (c) of the negative pressure wound therapy device relate to all aspects of the present invention, i.e., to the article of manufacture, to the device, to the use and to the method which are in accordance with the present invention.

Wound dressing (c) of the negative pressure wound therapy device of the present invention ("first wound dressing") must on no account be confused with that wound dressing of the present invention which is used for wound therapy in the second segment of therapy and is more particularly described hereinbelow ("second wound dressing"). However, it may be noted that the hereinbelow described wound dressings are in principle also useful as wound dressings (c) and are accordingly encompassed in the present invention.

The second segment of therapy is generally conducted "without negative pressure". This is not to be understood as meaning that a wound treatment is carried out with a negative pressure wound therapy device without applied negative pressure. On the contrary, it is to be understood as meaning that the use of a negative pressure wound therapy device is completely eschewed in the second segment of therapy.

The wound dressing ("second wound dressing") is generally a wound dressing that permits a wound treatment in a moist or moist-wet environment. Moist or moist-wet herein is to be understood as meaning that the wound under the wound dressing has a moist or moist-wet surface, i.e., the wound does not dry (or at least not completely) under the surface. The wound dressing ("second wound dressing") preferably comprises an absorbent body comprising a superabsorbent polymer.

In a particularly preferred embodiment, the (second) wound dressing comprises an absorbent body comprising an at least regionally liquid permeable envelope and the superabsorbent polymer disposed therein. In other words, the superabsorbent polymer is surrounded by the envelope.

The at least regionally liquid permeable envelope permits the passage of liquids over its entire area or at least in certain regions of the envelope. The envelope can consist of a single material or comprise two or more materials. At least on one side of the wound dressing which faces the wound in use, the envelope may advantageously be or comprise a textile (sheet) material, for example a drawn-loop knit, a formed-loop knit or a woven, especially of polyolefin, especially polypropylene. The envelope may advantageously consist at least partly of a textile fabric which is inelastically stretchable in longitudinal, transverse and diagonal directions, as disclosed in EP 0 594 034.

A superabsorbent polymer (SAP) is generally a water-insoluble, swellable polymer capable of absorbing a multiple of its own weight of a liquid, for example water. The absorption of liquid leads to the formation of a hydrogel. In the context of this invention, the term "superabsorbent polymer" refers particularly to a polymer which, when measured by standard test method WSP 240.2 (05), has a w value ("free swell capacity") of not less than 10 g/g, preferably not less than 20 g/g. The WSP 240.2 (05) test method for determining the w value is described in "Standard Test Methods for the Nonwovens and Related Industries", edition 2008 (issued by "EDANA, International Association Serving the Nonwovens and Related Industries", Cary, N.C., USA and "INDA, Association of the Nonwovens Fabrics Industry", Brussels, Belgium). WSP 240.2 (05) to EDANA is a standard test method for determining the w value ("free swell capacity") of superabsorbent polyacrylate powder. According to WSP 240.2 (05), the free swell capacity of a 0.9 weight percent saline is determined. In connection with the present invention, the determination of the w value of superabsorbent material other than polyacrylate powder is carried out in a corresponding manner.

The superabsorbent polymer can be in the form of fibers or preferably particles.

The superabsorbent polymer preferably is or comprises polyacrylate. Polyacrylate in the context of the present invention is to be understood as meaning a synthetic polymer which contains acrylic acid (2-propenoic acid, $CH_2=CH-CO_2H$) and/or a salt thereof as monomer. The monomer fraction is especially more than 70, for example more than 80 or 95 weight percent of acrylic acid and/or of a salt thereof (based on the overall weight of the polyacrylate). The polyacrylate can be present as homopolymer, copolymer or block polymer.

To achieve in the wound dressing an advantageous pH for wound treatment, ranging from about pH 4.0 to pH 8.5, especially between pH 5.0 and 6.0, the polyacrylate is preferably present as partially neutralized polymer, the degree of neutralization should be in particular between 20% and 90%, more preferably between 45% and 80%.

Particularly advantageous effects for wound healing can arise when the absorbent body comprises a mixture of polyacrylate particles, wherein the particle mixture contains polyacrylate particles in differing size, characterized in that the particle mixture contains
a) 5 to 100 wt %, preferably 5 to 98 wt % of particles having a particle size x where x<300 μm, and
b) 0 to 95 wt %, preferably 2 to 95 wt % of particles having a particle size x where x>300 μm.

The particle mixtures disclosed in WO2009/068249 are incorporated by reference herein with regard to further polyacrylate particle mixtures that can be used for the present invention with particular advantage.

Particle size in connection with the present invention is determined in line with EDANA 420.2-02, the sieves (200 mm in diameter) having hole sizes as specified. Sieves having other hole sizes such as, for example, 125 μm, 160 μm, 630 μm, 900 μm and 1500 μm can also be used. Dry polyacrylate particles having a moisture content of less than 10 wt % of water based on the overall weight of the particles are taken as the basis here, while the moisture content is determined in accordance with EDANA 450.2-02.

The absorbent body may further comprise a fibrous nonwoven web. The fibrous nonwoven web may serve as a support material for the swellable polymer.

The fibrous nonwoven web preferably comprises a fiber material which is hydrophilic. The fibers of this hydrophilic fiber material may be or comprise for example water-insoluble fibers of cellulose, for example largely delignificated industrial pulp fibers, for example woodpulp fibers, preferably having a fiber length of <5 mm. The fibrous nonwoven web may also contain or consist of hydrophilic fiber material of regenerated cellulose, carboxymethylcellulose, carboxyethylcellulose, hydroxymethylcellulose or hydroxyethylcellulose. It may also be based on or consist of a mixture of fibers of cellulose, regenerated cellulose, carboxymethylcellulose, carboxyethylcellulose, hydroxymethylcellulose or hydroxyethylcellulose and thermoplastic fibers, for example of polyethylene, polypropylene or polyester.

Preferably, the swellable/superabsorbent polymer is distributed in particulate form in the fibrous nonwoven web.

In a particularly preferred embodiment, the absorbent body comprises at least one superabsorbent polyacrylate plus a fibrous nonwoven web comprising a mixture of cellulose fibers and polypropylene fibers or based thereon. The fibrous nonwoven web can serve as support material. The fibers can be processed together with particles or fibers of the superabsorbent polymer by an air-laid process to form a layer.

In a particularly preferred embodiment, the absorbent body comprises an enveloped air-laid layer comprising a superabsorbent polyacrylate, cellulose fibers and polypropylene fibers.

In a preferred embodiment, a solution is applied to the absorbent body. Application is preferably taken to the point of saturation and is preferred to be done with an aqueous solution which allows the swellable/super-absorbent material to swell and transition into a gel-like state. The aqueous solution is preferably salt-containing.

The absorbent body may be impregnated with, for example, not less than 600 weight percent, not less than 800 weight percent or not less than 1000 weight percent of an aqueous solution, based on the weight of the dry absorbent body. The absorbent body further preferably has applied to it less than 5000 weight percent, for example less than 3500 weight percent, for example less than 2500 weight percent of an aqueous solution.

In a particularly preferred embodiment, the absorbent body contains that amount of an aqueous activating solution which corresponds to its maximum absorption capacity for Ringer's solution. The maximum absorption capacity for Ringer's solution can be determined in accordance with the aforementioned test method WSP 240.2 (05), except that a) Ringer's solution is used instead of the saline used in WSP 240.2 (05) and b) the absorbent body of the present invention is used instead of the envelope-sealed test substance ("bag" in paragraph 6.1 of WSP 240.2 (05)). The maximum absorption capacity corresponds to the weight difference, determined gravimetrically by this method, between the dry absorbent body and the activated absorbent body, with a discrepancy in weight difference by 15% up or down being encompassed.

The aqueous solution is a synthetic solution and comprises no bodily fluids/body-secreted fluids. Preferably, the aqueous solution contains more than 50, for example more than 70, more than 80, more than 90 or 100 volume percent of water. It can contain not less than 5 mmol/l of sodium ions, not less than 0.1 mmol/l of potassium ions, not less than 0.1 mmol/l of calcium ions and/or not less than 5 mmol/l of chloride ions. Optionally, the aqueous solution contains further inorganic cations and/or anions, optionally organic anions, and also optionally additional bio-organic compounds. The pH is preferably from 4 to 9. The viscosity at 20° C. is preferably between 0.8 mPa·s and 150 mPa·s. The viscosity of the solution is determined using a Brookfield viscometer (units: 1 Pa·s=1 Ns/m$^2$).

Preferably, the aqueous solution comprises or is a Ringer solution. A Ringer solution is a synthetic solution which is approximately iso-osmotic with blood and which comprises sodium chloride, potassium chloride and calcium chloride dissolved in distilled water. Preferably, the Ringer solution contains 147 mmol/l of sodium ions, 4.0 mmol/l of potassium ions, 3.0 mmol/l of calcium ions and 157 mmol/l of chloride ions, although a discrepancy of 5% between the particular ion concentration and the specified value is possible.

One advantage of the solution-impregnated absorbent body is that the wound is maintained in a moist environment and does not dry out right from the start of therapy, which promotes wound healing.

In a further embodiment, the absorbent body may comprise an antimicrobial substance, for example in lieu of or in addition to the aqueous solution described above. Preferably, the antimicrobial substance is or comprises a substance with an antimicrobial effect which is in cationic form at pH 4-7.5, for example substances having amino or imino groups. The cationic antimicrobial substance may concern antimicrobially efficacious metal cations, especially silver cations, for example a complex of 1-vinyl-2-pyrrolidone with silver cations. Cationic substances with an antimicrobial effect which are particularly suitable include biguanide derivatives such as chlorhexidine or polybiguanides, such as polyethylene biguanide (PEB), polytetramethylene biguanide (PTMB) or polyethylene hexamethylene biguanides (PEHMB). Polyhexamethylene biguanide (PHMB, or polyhexanide) is a particularly preferred polybiguanide. Suitable cationic substances having an antimicrobial effect further include polyguanidines such as, for example, polyhexamethylene guanidines (PHMG), N-octyl-1-[10-(4-octyliminopyridin-1-yl)decyl]pyridin-4-imine (octenidine), quaternary ammonium compounds, for example benzalkonium chloride or cetylpyridinium chloride, triazines such as, for example, 1-(3-chloroallyl)-3,5,7-triaza-1-azonia-adamantane chloride or the ammonium compound taurolidine.

In addition to the above-described absorbent body, the (second) wound dressing of the present invention can contain a wound contact layer and an evaporation inhibiting backlayer. In a preferred embodiment, therefore, the wound dressing comprises i) an atraumatic wound contact layer,
ii) the absorbent body and
iii) a preferably evaporation inhibiting film layer on the wound remote side.

Said wound contact layer (i) preferably concerns an atraumatic effect coating applied partially and/or texturedly. The coating may be applied directly to the absorbent body. It is preferably applied to an absorbent body surrounded with the above-described textile envelope. The coating is preferably a silicone coating, and the coating may be, for example, porous and formed by a plurality of comparatively thin strips or lines or island-shaped regions, which can be separated from each other by uncoated regions. In these uncoated regions, the wound-facing side of the absorbent body can be exposed to the wound. The atraumatic effect coating can thus form a projection to prevent the absorbent body sticking to the wound tissue and maintain a certain small gap between the wound-facing side of the absorbent body and the wound tissue. Thus, the porous enveloping layer material can remain three-dimensionally open and provide or maintain a lower resistance to liquid passage in both directions throughout the in-use period of the wound dressing.

The wound remote side of the absorbent body can be covered by a foil, preferably a polymeric foil. The foil is preferably in essence impervious to germs and water and thus offers improved evaporation control.

The wound dressing can be applied atop a wound or else be used for packing out deep wounds.

The above considerations regarding preferred embodiments of the wound dressing, in particular the second wound dressing, relate to all aspects of the present invention.

The present invention is especially advantageous when the wounds are burn wounds; wounds caused by mechanical traumatization; a wound caused by the action of chemicals; a wound caused by a metabolic disorder; a wound caused by disrupted blood circulation; or a wound caused by a pressure ulcer.

The following examples illustrate the advantages of the present invention together with FIGS. 1 to 4.

EXAMPLES

Example 1

Improvement of Wound Healing

Eight dermoepidermal wounds about 3.5 cm in diameter per test were inflicted on pigs in the region of the dorsal adipose tissue. A first experimental series, hereinafter referred to as treatment 1, comprised 8 days of purely negative pressure therapy, while a second experimental series, treatment 2, comprised a first segment of therapy involving 4 days of negative pressure therapy, immediately followed by a second segment of therapy involving 4 days of therapy in a moist/moist-wet environment. A third experimental series, treatment 3, comprised a first segment of therapy involving 6 days of negative pressure therapy, immediately followed by a second segment of therapy involving 2 days of therapy in a moist/moist-wet environment. The second segment of therapy utilized TenderWet® Plus wound dressing (Paul Hartmann AG), while negative pressure therapy utilized polyurethane film (Hydrofilm®, Paul Hartmann AG) as covering material (a) and open-cell foam as wound dressing (c) (Vivanomed®, Paul Hartmann AG) together with a commercially available adapter, tube (fluid communication means b) and vacuum unit.

Figure 1:
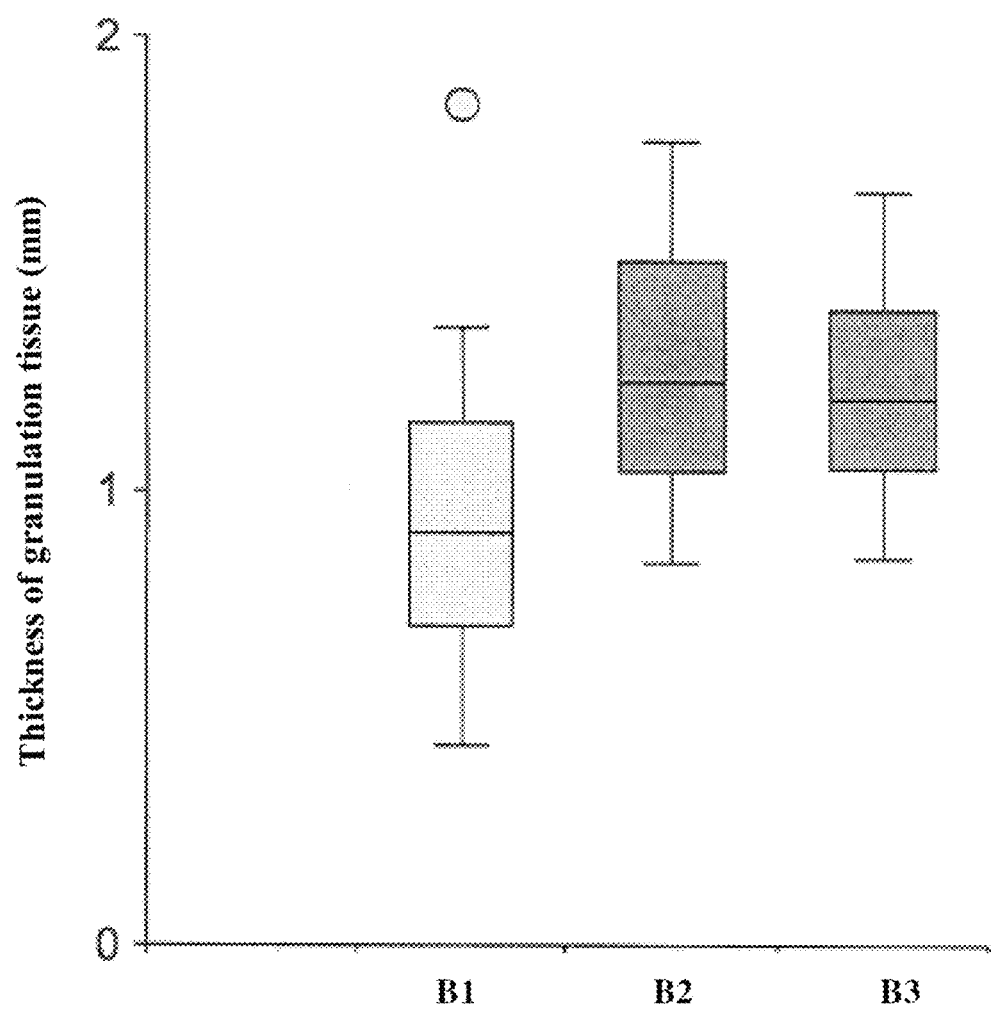
FIG. 1 illustrates formation of granulation tissue for the invention (B2, B3) in relation to negative pressure therapy (B1).

FIG. 1 shows that inventive treatments B2 (4 days of negative pressure+4 days of moist environment) and B3 (6 days of negative pressure+2 days of moist environment) produced an appreciable improvement in the formation of granulation tissue over negative pressure therapy B1 of the same duration (8 days).

FIG. 2 shows that inventive treatments B2 (4 days of negative pressure+4 days of moist environment) and B3 (6 days of negative pressure+2 days of moist environment) produced an improvement in neovascularization over negative pressure therapy B1 of the same duration (8 days). The improvement achieved in the stimulation of neovascularization was appreciable.

FIG. 3 shows that inventive treatments B2 (4 days of negative pressure+4 days of moist environment) and B3 (6 days of negative pressure+2 days of moist environment) produced an improvement in the formation of fibroblasts compared to negative pressure therapy B1 of the same duration (8 days). An appreciable increase in fibroblast density was achieved.

The positive effects due to the therapy scheme of the present invention which are shown in FIGS. 1 to 3 were unforeseeable by a person skilled in the art.

Example 2

Scavenging of Inflammation Mediators by Polyacrylate-Containing Wound Dressings

A whole series of proteins which hinder wound healing directly or indirectly have been described in wounds with disrupted or problematic healing. They include DAMPs and PAMPs but also matrix metalloproteinases and other proteins. Therefore, these mediators should be removed from the wound preferentially—particularly in hyperinflammatory states. This removal can take place with advantage in the treatment scheme of the present invention, as demonstrated by the following test:

Wound exudate was isolated from chronic wounds (Eming et al., 2008). The amount, which corresponds to 50 micrograms of total protein, was incubated with 100 mg of FAVOR® PAC 300 superabsorbent (preswollen with Ringer solution to saturation) for 2 hours. Thereafter, the liquid was separated from the superabsorbent, the superabsorbent was washed 2 times with an excess of Ringer solution and the bound proteins were dissolved with SDS sample buffer (10 mg of SDS dissolved in 0.25 mL of 0.5 M Tris/HCl, pH 6.8, 0.115 mL of glycerol (87%), 0.5 mL of $H_2O$ and 1-2 drops of bromophenol blue (1% in water)). The proteins were separated according to their molecular weight in a 10% polyacrylamide gel (Eckert and Kartenbeck: *Proteine: Standardmethoden der Molekular-und Zellbiologie: Präparation, Gelelektrophorese, Membrantransfer und Immundetektion*. Springer, Berlin, 1997, ISBN-10: 3540612785). Following transfer to a PVDF membrane and immunological detection with specific affinity-purified antibodies (Calgranulin A Antibody (C-10), sc-48352; Calgranulin B Antibody (C-19), sc-8114; Santa Cruz Biotechnology, Inc., Bergheimer Str. 89-2, 69115 Heidelberg, Germany) in accordance with the manufacturer's instructions, the following picture presented itself, see FIG. 4:

the left-hand lane is the wound fluid before incubation;
the middle lane is the wound fluid after incubation;
the right-hand lane is the protein bound by the FAVOR® PAC 300 superabsorbent.

After immunodetection, the corresponding bands S100A8 and S100A9 are clearly visible and the amount of bound S100A8 and S100A9 protein shows clear binding to the polyacrylate polymer. Removal of the mediators is thus an unexpected effect which can contribute to the clinical success of the treatment scheme according to the present invention.

The invention claimed is:

1. A method for treatment of a wound on the human or animal body by therapy, said method comprising
   i) a first segment of therapy, in which negative pressure wound therapy is conducted using a device for negative pressure wound therapy comprising a first wound dressing, wherein the first segment of therapy is terminated before visible granulation,
   and
   ii) a subsequent, second segment of therapy, which is conducted using a second wound dressing without creating a negative pressure wherein said second wound dressing comprises an absorbent body comprising a superabsorbent polymer and wherein said absorbent body is impregnated with a solution, wherein the second segment of therapy follows immediately on from the first segment of therapy.

2. The method for treatment of claim 1, wherein said first segment of therapy comprises
   (a) applying the first wound dressing to the wound,
   (b) applying an air impermeable covering material to form an airtight enclosure of the wound and its surroundings to form a wound space,
   (c) providing fluid communication between said wound space and a negative pressure source outside said wound space so that a negative pressure can be established in said wound space and liquids can be aspirated out of said wound space, (d) establishing negative pressure in said wound space.

3. The method of claim 1, wherein the wound is characterized by inflammation or edema.

4. The method of claim 1, wherein the second wound dressing effects an enhanced stimulation of formation of granulation tissue, an enhanced stimulation of neovascularization, and/or an enhancement in the fibroblast density in the surficial granulation tissue of the wound.

5. The method of claim 1 wherein said first segment of therapy extends over a period of 1 to 8 days.

6. The method of claim 1 wherein said second segment of therapy extends over a period of 1 to 20 days.

7. The method of claim 1 wherein said absorbent body comprises a liquid permeable textile envelope with the superabsorbent polymer disposed therein.

8. The method of claim 1 wherein said superabsorbent polymer is or comprises polyacrylate.

9. The method of claim 1 wherein said second wound dressing comprises:
　i) an atraumatic wound contact layer,
　ii) the absorbent body and
　iii) an evaporation inhibiting film layer on the wound remote side.

10. The method of claim 1 wherein said absorbent body comprises a fibrous nonwoven web.

11. The method of claim 10 wherein the fibrous nonwoven web comprises cellulose fibers.

12. The method of claim 1 wherein said absorbent body is impregnated with Ringer's solution.

13. The method of claim 1 wherein said second segment of therapy involves a moist to moist-wet environment of the wound.

14. The method of claim 1 wherein said absorbent body comprises an antimicrobial substance.

15. The method of claim 1 wherein the device for conducting the negative pressure wound therapy comprises
　(a) an air impermeable covering material for airtight enclosure of the wound and its surroundings to form a wound space,
　(b) means for providing fluid communication between said wound space and a negative pressure source outside said covering material so that a negative pressure can be established in said wound space and liquids can be aspirated out of said wound space, and
　c) said first wound dressing, which facilitates an essentially uniform distribution of said negative pressure in said wound space.

16. The method of claim 1 wherein the wound is a burn wound, a wound caused by mechanical trauma, a wound caused by the action of chemicals, a wound caused by a metabolic disorder, a wound caused by disrupted blood circulation, or a wound caused by a pressure ulcer.

17. A kit of parts comprising a device for negative pressure wound therapy and a second wound dressing, for use in the treatment of wounds on the human or animal body by therapy, wherein said second wound dressing comprises an absorbent body comprising a superabsorbent polymer, wherein said treatment comprises a first segment of therapy, in which negative pressure wound therapy is conducted using said device, and a subsequent, second segment of therapy which is conducted using said second wound dressing without creating a negative pressure, said kit further comprising instructions for carrying out the method of claim 1.

18. A method for treatment of a wound on the human or animal body by therapy, said method comprising
　i) a first segment of therapy, in which negative pressure wound therapy is conducted using a device for negative pressure wound therapy comprising a first wound dressing, and
　ii) a subsequent, second segment of therapy, which is conducted using a second wound dressing without creating a negative pressure wherein said second wound dressing comprises an absorbent body comprising a superabsorbent polymer and wherein said absorbent body is impregnated with a solution,
　wherein said second segment of therapy commences during or immediately following an inflammatory phase.

19. The method of claim 18 wherein said absorbent body is impregnated with Ringer's solution.

20. The method of claim 18 wherein said second segment of therapy involves a moist to moist-wet environment of the wound.

* * * * *